United States Patent
Mohamed et al.

(10) Patent No.: US 9,452,297 B2
(45) Date of Patent: Sep. 27, 2016

(54) HYBRID INFRA-RED LASER AND PULSED ELECTROMAGNETIC MEDICAL APPARATUS AND METHODS OF USE

(71) Applicants: Hossam Abdel Salam El Sayed Mohamed, Ottawa (CA); Houda Abdul Rahman M. Al Mansour, Ottawa (CA)

(72) Inventors: Hossam Abdel Salam El Sayed Mohamed, Ottawa (CA); Houda Abdul Rahman M. Al Mansour, Ottawa (CA)

( * ) Notice: Subject to any disclaimer, the term of this patent is extended or adjusted under 35 U.S.C. 154(b) by 0 days.

(21) Appl. No.: 14/611,726

(22) Filed: Feb. 2, 2015

(65) Prior Publication Data

US 2016/0074670 A1 Mar. 17, 2016

Related U.S. Application Data

(63) Continuation of application No. PCT/IB2014/001849, filed on Sep. 12, 2014.

(51) Int. Cl.
| | | |
|---|---|---|
| *A61B 17/52* | (2006.01) | |
| *A61N 2/00* | (2006.01) | |
| *A61N 2/02* | (2006.01) | |
| *A61N 5/06* | (2006.01) | |
| *A61N 5/067* | (2006.01) | |

(52) U.S. Cl.
CPC ............... *A61N 2/002* (2013.01); *A61N 2/02* (2013.01); *A61N 5/0613* (2013.01); *A61N 2005/067* (2013.01); *A61N 2005/0659* (2013.01)

(58) Field of Classification Search
CPC ...... A61N 2/002; A61N 2/02; A61N 5/0613; A61N 2005/0659; A61N 2005/067
USPC ................................ 600/9–14; 128/897–899
See application file for complete search history.

(56) References Cited

U.S. PATENT DOCUMENTS

| | | | | |
|---|---|---|---|---|
| 6,450,941 B1 * | 9/2002 | Larsen | ............... | A61N 1/40 600/14 |
| 6,553,161 B1 * | 4/2003 | Upton | ............... | G02B 6/4227 385/25 |
| 7,722,655 B2 * | 5/2010 | Lee | ............... | A61H 7/003 607/88 |
| 2003/0093915 A1 * | 5/2003 | Pearl | ............... | A61N 5/0617 34/96 |
| 2005/0075703 A1 * | 4/2005 | Larsen | ............... | A61N 1/40 607/88 |

FOREIGN PATENT DOCUMENTS

RU 2104067 C1 2/1998

OTHER PUBLICATIONS

English language translation of RU 2104067 C1 (1998).
International Search Report of PCT Application No. PCT/IB2014/001849, dated May 19, 2015.

* cited by examiner

*Primary Examiner* — Navin Natnithithadha
*Assistant Examiner* — Sunita Reddy
(74) *Attorney, Agent, or Firm* — Caesar Rivise, PC

(57) ABSTRACT

Apparatus and methods for simultaneously providing an infra-red laser beam and a concentrated uni-polar, pulsed electromagnetic field to a region of interest in the body of a patient are disclosed. The apparatus produces the infrared laser beam from a laser diode and the pulsed electromagnetic field from an electrically conductive coil. The infra-red laser beam and the pulsed electromagnetic field are produced concurrently along a common axis. A focusing magnet is provided to concentrate the lines of flux so that they extend along the laser beam. The apparatus includes a body of Mu-metal shielding surrounding the components of the apparatus except for one pole of the coil from which the lines of flux of the electromagnetic field extend to further concentrate the field and render it effectively uni-polar.

16 Claims, 1 Drawing Sheet

HYBRID INFRA-RED LASER AND PULSED ELECTROMAGNETIC MEDICAL APPARATUS AND METHODS OF USE

CROSS-REFERENCE TO RELATED APPLICATIONS

This bypass continuation application claims priority under 35 U.S.C. §120 of international patent application PCT/IB2014/001849 filed on Sep. 12, 2014 and whose entire disclosure is incorporated by reference herein.

FIELD OF THE INVENTION

This invention relates generally to medical devices and methods of use and more particularly to apparatus making use of an Infra-red Laser and a Pulsed Electromagnetic Field and methods of use for treating various medical conditions.

BACKGROUND OF THE INVENTION

The therapeutic application of Pulsed Electromagnetic Field ("PEMF") therapy has been accepted by the Food and Drug Administration for use in humans and has become an accepted modality in treating various medical conditions. Typically PEMF therapy is achieved by means of apparatus making use of at least one inductive coil producing a pulsating electromagnetic field. The coil(s) is/are energized by applying a predetermined electrical current to the coil(s) in order to produce a desirable magnetic field with specified field characteristics.

Infra-red radiation also has many benefits to the human body and there are many clinics that use infra-red for treatment of aging process and its related complications. The problem is that infra-red cannot penetrate deep tissues. Historically its main use for therapeutic purposes has been directed to skin and the very near subcutaneous tissues. However, the introduction of pulsed infra-red laser that can penetrate deeper tissues has enabled the treatment of other conditions involving deeper tissue penetration.

While each of those modalities offers beneficial, e.g., therapeutic, effects, it is believed that their combination will offer even a greater, i.e., synergistic, effect. Accordingly, the subject invention is directed to apparatus and methods for providing infra-red radiation therapy concurrently with PEMF therapy.

SUMMARY OF THE INVENTION

In accordance with one aspect of the invention there is provided apparatus for applying infra-red laser radiation and pulsed electromagnetic energy to an anatomic region of interest located within the body of a patient. The apparatus basically comprises a housing, an infra-red laser, a coil of electrically conductive material, a focusing magnet, a body of Mu-metal shielding, an electrical power supply, and a computer processor. The infra-red laser is located within the housing and is arranged for providing a collimated infra-red laser beam along an axis. The coil is disposed within the housing surrounding the laser beam and is arranged when electrically energized to create a pulsed electromagnetic field extending along the axis of the laser beam. One end portion of the coil establishes a first electromagnetic pole and another end portion of the coil establishes a second electromagnetic pole. The second electromagnetic pole is of opposite polarity to the first electromagnetic pole. The axis of the laser beam extends through the first and second poles, with lines of flux of the magnetic field extending outward from the first pole generally parallel to the longitudinal axis. The focusing magnet is disposed within the housing adjacent the first pole of the coil to encircle the laser beam. The focusing magnet includes a first pole of a first polarity and a second pole of a second polarity. The first pole of the focusing magnet is located radially inward of a second pole of the focusing magnet and is the same polarity as the first pole of the coil to thereby concentrate the lines of flux of the electromagnetic field along the axis of the laser beam. The body of Mu-metal shielding surrounds the coil and the focusing magnet except for the first pole of the focusing magnet so that the first pole of the focusing magnet is exposed and from which the lines of flux of the magnetic field and the laser beam emanate.

Other aspects of this invention entail various methods of treating medical conditions of a patient by applying the infra-red laser beam and the pulsed electromagnetic field to a region of interest in the body of that patient. Those methods basically comprise providing apparatus similar to that described above, disposing the apparatus adjacent the region of interest of the patient and operating the apparatus to produce the infra-red laser beam and the pulsed electromagnetic field and direct both concurrently to a region of interest in the body of that patient.

DETAILED DESCRIPTION OF THE PREFERRED EMBODIMENT

Figure 1:
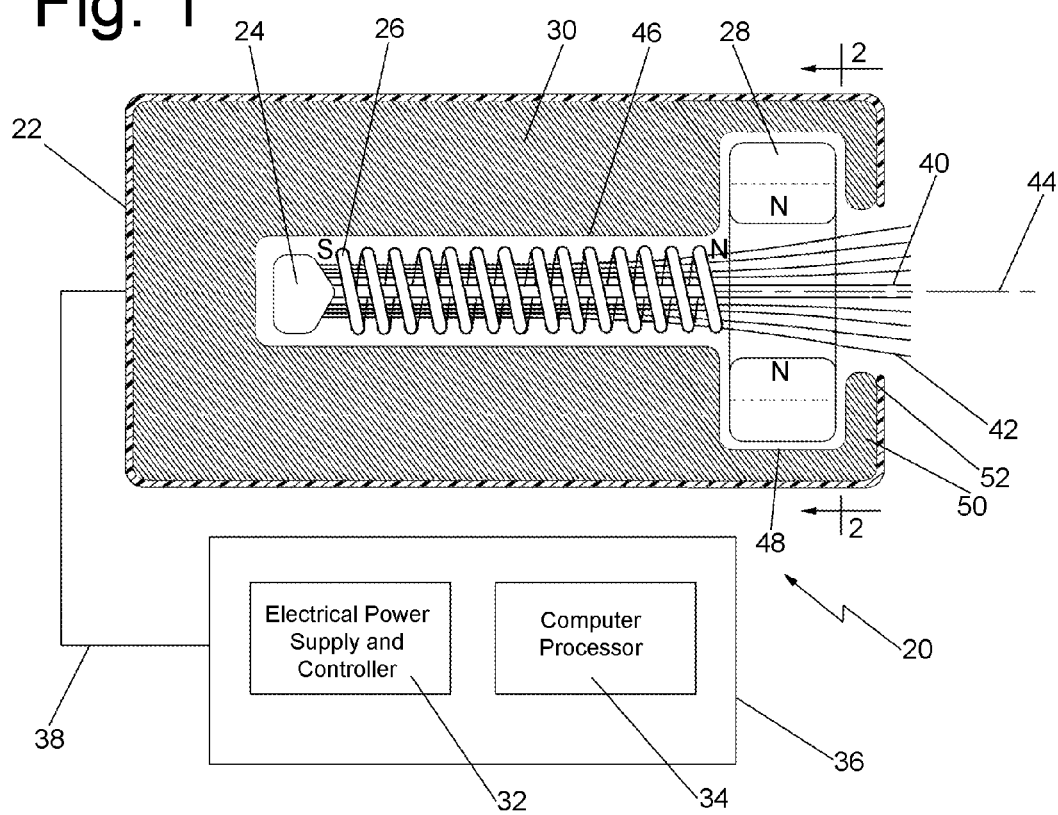
FIG. 1 is a partial cross-sectional view of one exemplary embodiment of a hybrid apparatus for providing both Infrared laser radiation therapy and PEMF therapy constructed in accordance with this invention.
Figure 2:
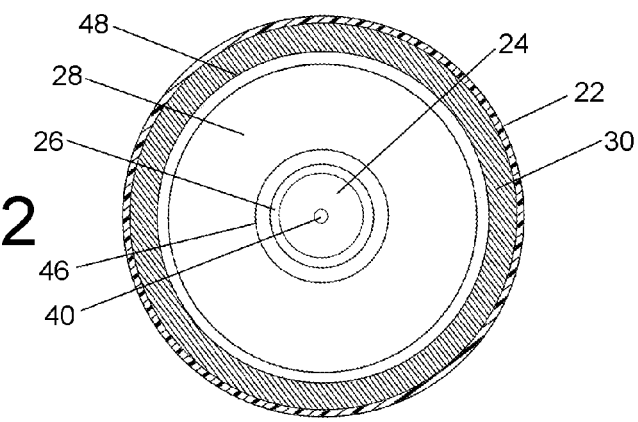
FIG. 2 is a sectional view of the apparatus of FIG. 1 taken along line 2-2 thereof.

Referring now to the various figures of the drawing wherein like reference characters refer to like parts, there is shown in FIG. 1 at 20 apparatus for concurrently producing an infra-red laser beam and a collimated (or otherwise concentrated) uni-polar pulsed electromagnetic field (PEMF) to the body of a patient to provide therapy to an anatomic region of interest therein. It is believed that the combination of those two modalities applied concurrently will provide a synergistic effect. In particular, infra-red laser therapy and PEMF therapy each have a good response in the treatment of the same groups of diseases. The mechanism of action of both infra-red laser therapy and PEMF therapy is believed to be through mitochondrial and regenerative medicine pathways. The mitochondrial mechanism is achieved via application of external energy that can be utilized by the tissues to compensate for energy deficit produced from the mitochondria. The regenerative medicine mechanism is that both infra-red laser and PEMF can activate stem cells. Moreover, an externally applied PEMF can control the orientation of the hydrogen atoms of water of the patient's tissues in the region of interest thereby concentrating the infra-red energy applied to those tissues by the laser beam. Thus, it is believed that the combination of an infra-red laser beam along with a PEMF, particularly a unipolar PEMF, has a synergistic effect.

Turning now to FIG. 1, it can be seen that the apparatus 20 basically comprises a housing 22, an infra-red laser diode 24, a coil 26 of electrically conductive material, a focusing magnet 28, a body of Mu-metal shielding 30, an electrical power supply/controller 32, and a computer processor 34. All of the foregoing components except for the electrical power supply/controller 32 and the computer processor 34 are located within the housing 22. The electrical power supply/controller 32 and the computer processor 34 are located in a separate housing 36 and are electrically connected to the infra-red laser diode 24 and the coil 26 via an electrical cable 38. Power for the electrical power supply/controller 32 and the computer processor 34 is provided via a conventional plug (not shown) adapted to be connected to a 110 volt wall outlet (not shown). The power supply/controller 32 provides electrical power to the laser diode 24 to cause it to emit an infra-red laser beam 40, whose frequency and intensity is established by the computer processor 34. The power supply/controller 32 also provides electrical power to the coil 22 to cause it to produce a pulsed electromagnetic field (PEMF) 42.

It should be pointed out at this juncture that, if desired, all of the components of the apparatus 20 can be located within the housing 22 instead of being in separate housings. In any case, the housing 22 is preferably sufficiently compact so that it can be hand-held by a user to direct the infra-red laser beam 40 and the PEMF 42 produced by its components to a region of interest in the body of a patient for some therapeutic or other beneficial purpose. The housing 22 can be formed of any suitable material, e.g., plastic.

The infra-red laser diode 24 can be of any suitable construction, e.g., like those conventionally used in the prior art for effecting infra-red radiation therapy, and is mounted in the housing 22 so that the infra-red laser beam 40 produced by it extends along a longitudinal axis 44 and projects out of one end of the housing 22 as shown in FIG. 1.

In accordance with one exemplary embodiment of this invention the apparatus is arranged to produce an infra-red laser beam which is pulsed at a frequency in the range of 50,000 Hz to 100,000 Hz, with the power of the laser beam being in the range of 25-50 watts.

The coil 26 basically comprises a helical member made up of one or plural electrical conductors wound in a helix. The coil is located within the housing adjacent the laser diode 24 so that its central longitudinal axis is coincident with the axis 44 of the laser beam 40 produced by the diode. The conductor(s) of the coil is/are coupled to the electrical power supply/controller 32 so that when energized the coil produces the electromagnetic field 42 having flux lines centered about and extending along the longitudinal axis 44. In the exemplary embodiment shown the South (S) pole of the coil 26 is located adjacent the laser diode 24 and the North (N) pole of the coil is at the opposite end, e.g., adjacent the end of the housing from which the laser beam emanates. If desired, the poles of the coil can be reversed, provided that the poles of the focusing magnet are oriented appropriately, as will be discussed later. In any case, the coil surrounds the infra-red beam so that the passage of the beam is unobstructed through the housing.

In the exemplary embodiment shown in the drawing the focusing magnet 28 is a permanent magnet which is ring or circular shaped. The North (N) and South (S) poles of the magnet are oriented radially with respect to each other. In the exemplary embodiment the North pole is located at the innermost portion of the magnet, while the South pole is at the outermost (peripheral) portion of the magnet. The magnet 28 produces a very strong magnetic field which serves to focus or collimate the lines of flux of the field emanating from the North pole of the coil 26. In particular, the lines of flux from the field produced at the North pole of the focusing magnet 28 repel the lines of flux produced by the North pole of the coil (which would tend to splay or spread out), thus causing the lines of flux of the field 42 to become more concentrated or collimated. This concentration helps the electromagnetic field 42 go for a longer distance before spreading out further to enable deeper tissue penetration. The combination of deeper tissue penetration with high concentration means more efficient energy delivery to the tissues at the region of interest.

In addition to the shaping of the field 42 provided by the focussing magnet 28, the PEMF field 42 is also shaped and collimated by the body of Mu-metal shielding 30. In particular, the body of Mu-metal 30 is located within the housing 22 and has a circular bore 46 in which the laser diode 24 and the coil 26 are located. A portion 48 of the bore 46 opposite the position of the diode is of enlarged internal diameter and serves to hold the ring shaped focussing magnet 28 therein. The end portion of the Mu-metal body includes a radially extending wall 50 covering the end of the focussing magnet, and has an opening 52 through which the laser beam 40 and the lines of flux of the PEMF 42 emanate for direction to the region of interest in the patient to be treated. With the Mu-metal body 30 shaped and located as described above, the lines of flux of the field 42 produced by the coil are concentrated or collimated by the surrounding Mu-metal so that those lines of flux extend generally parallel to the central longitudinal axis 40 for a substantial distance beyond the end of the housing as shown in FIG. 1 to apply the pulsed magnetic energy to the region of interest.

It should be noted that while the lines of flux produced by the coil 26 do, in fact, curve back to the coil's South pole, they are shaped and confined by the Mu-metal shield so that their effect on the region of interest is minimal, if any. Thus, the inclusion of the Mu-metal shield 30 results in the production of a magnetic field emanating from the apparatus 20 which is effectively uni-polar.

As mentioned above, in the exemplary embodiment shown in FIG. 1, the uni-polar magnetic field is of North polarity, i.e., it consists of the concentrated lines of flux from the North pole of the coil, since for many therapies it is desired to utilize the North pole as the treating modality, inasmuch as the North pole seems to provide better physiological effects on human cells. Thus, in the exemplary embodiment the apparatus 20 is arranged to have the North poles of the coil 26 exposed, with the South pole of the coil being shielded by the Mu metal body 30. For other applications, the South pole of the apparatus 20 may be utilized. In such a case the South pole of the coil will be exposed, with the Mu metal body 30 surrounding the North pole of the coil and the poles of the focusing magnet 28 will be reversed, i.e., the North pole of the focusing magnet will be on the outer periphery of the focusing magnet.

In accordance with a preferred embodiment of this invention the electrical energy applied to the coil is pulsed at a frequency in the range of 11 Hz to 30 Hz basis to produce the PEMF 42. To that end, there will be a "on" time period during each cycle of operation of the apparatus wherein the magnetic flux emanating from the apparatus impinges the anatomic region of interest in the patient, thereby applying magnetic energy to that region, and an "off" time period during each cycle when no magnetic flux from the coil will reach the anatomic region of interest. The computer processor 34 is arranged to establish the "on" and "off" time periods of the duty cycle of operation of the apparatus 20 (i.e., the time that the region of interest is exposed to the collimated magnetic field). In accordance with a preferred exemplary embodiment of this invention the ratio of the on-to-off periods of time is preferably in the range of 50%-70% on and 50%-30% off, at an on-off pulse rate of approximately 11 to 30 per second. The above ranges are merely exemplary and other duty cycles can be utilized depending upon conditions. The intensity of the PEMF can be whatever is deemed appropriate for the application, e.g., approximately 600 Gauss or less.

Use of the apparatus of this invention, like the exemplary apparatus 20 (or any other apparatus constructed in accordance with this invention) for providing various therapies in accordance with this invention will now be described. For example, the exemplary apparatus 20 of FIG. 1 can be used for treating a brain disorder or condition. To that end, the apparatus 20 is disposed adjacent the skin of the patient at a desired position adjacent the patient's skull and juxtaposed and oriented so that the portion of the housing 22 from which the infra-red laser and the unipolar PEMF emanate along axis 44 is directed to region of interest in the patient brain to treat the particular pathology. When the apparatus 20 is in the desired position and orientation the apparatus may be activated (turned on). This can be accomplished by pressing an ON/OFF switch or button (not shown) on the apparatus' housing 22 to energize the laser diode 24 and to simultaneously energize the coil 26. Thus, the infra-red laser beam 40 and the uni-polar PEMF 42 will be produced concurrently along axis 44 so that they are directed to the region of interest in the patient's skull to penetrate through the skin and underlying tissue and bone of the skull to the situs of the pathology.

In closing it should be noted that the particular components and their arrangements as discussed above and as shown in the drawing are merely exemplary. Thus, other components can be used in lieu of those disclosed. By way of example, and not limitation, the shield 30 may be formed of some material having similar magnetic field modifying effects as Mu-metal. Moreover, the focussing magnet 28 may be in the form of a plurality of permanent magnets arranged in a ring-line configuration surrounding the axis of the laser beam, so long as the portion of those magnets closest to the end of the coil from which the PEMF emanates is of the same polarity as that end of the coil. Moreover, it is also contemplated that the focussing magnet may be an electromagnet instead of a permanent magnet. Further still, while the apparatus is preferably sufficiently small so that it can be hand-held by a user, it can, if desired, be supported by some mount, e.g., an adjustable member. Lastly, while it is preferable that the laser and the electromagnetic field each be pulsed, either or both, need not be pulsed for a particular application, e.g., treatment of the skin or other closely located tissue.

Without further elaboration the foregoing will so fully illustrate our invention that others may, by applying current or future knowledge, adopt the same for use under various conditions of service.

We claim:

1. An apparatus for applying infra-red laser radiation and pulsed electromagnetic energy to an anatomic region of interest located within the body of a patient, said apparatus comprising: a housing, an infra-red laser diode, a coil of electrically conductive material, a focusing magnet, a body of Mu-metal shielding, an electrical power supply, and a computer processor, said housing having a longitudinal axis, said infra-red laser diode being located within said housing and configured for providing a collimated infra-red laser beam along said axis, said coil being disposed within said housing, said coil surrounding said axis and configured to create a pulsed electromagnetic field having lines of flux extending along said axis, said coil having one end portion establishing a first electromagnetic pole and another end portion establishing a second electromagnetic pole, said second electromagnetic pole being of opposite polarity to said first electromagnetic pole, said axis extending longitudinally through said first and second poles, with said lines of flux of said magnetic field extending outward from said first pole and extending generally parallel to said axis, said focusing magnet being disposed within said housing adjacent said first pole of said coil to encircle said axis, said focusing magnet including a first pole of a first polarity and a second pole of a second polarity, said first pole of said focusing magnet being located radially inward of said second pole of said focusing magnet, said first pole of said focusing magnet being of the same polarity as said first pole of said coil to concentrate said lines of flux of said electromagnetic field along said axis, said body of Mu-metal shielding surrounding said coil and said focusing magnet except for said first pole of said focusing magnet, wherein said first pole of said focusing magnet is exposed, and whereupon said lines of flux of said magnetic field are concentrated along said axis of said laser beam.

2. The apparatus of claim 1 wherein said focusing magnetic comprises a ring-shaped permanent magnet.

3. The apparatus of claim 2 wherein said first pole of said coil and said first pole of said focusing magnet are each a North pole.

4. The apparatus of claim 1 wherein said first pole of said coil and said first pole of said focusing magnet are each a North pole.

5. The apparatus of claim 1 wherein said body of Mu-metal shielding is located within said housing and also surrounding said laser diode.

6. The apparatus of claim 1 wherein said infra-red laser beam is pulsed.

7. The apparatus of claim 6 wherein said infra-red laser beam is pulsed at a frequency in a range of 50,000 Hz to 100,000 Hz.

8. The apparatus of claim 7 wherein the power of said laser beam has a power in a range of from 25 to 50 watts.

9. The apparatus of claim 6 wherein said laser beam has a power in a range of from 25 to 50 watts.

10. The apparatus of claim 1 wherein said pulsed electromagnetic field is pulsed at a frequency in a range of 11 Hz to 30 Hz.

11. The apparatus of claim 10 wherein said pulsed electromagnetic field approximately has an intensity of 600 Gauss.

12. The apparatus of claim 1 wherein said pulsed electromagnetic field has an intensity of approximately 600 Gauss.

13. The apparatus of claim 1 wherein said processor is coupled to said electrical power supply and configured to control an intensity and a frequency of said infra-red laser beam.

14. The apparatus of claim 1 wherein said processor is coupled to said electrical power supply and configured to control an intensity and a frequency of said pulsed electromagnetic field.

15. The apparatus of claim 13 wherein said processor is coupled to said electrical power supply and configured to control the intensity and frequency of said pulsed electromagnetic field.

16. The apparatus of claim 1 wherein said apparatus is configured to be manually held by a user.

* * * * *